United States Patent
Kay et al.

(10) Patent No.: US 8,540,731 B2
(45) Date of Patent: Sep. 24, 2013

(54) SKIN TREATING DEVICE

(75) Inventors: Peter Kay, Warwick (GB); Libby Marshall, Warwick (GB); Clive Southernwood, Warwick (GB)

(73) Assignee: LRC Products Limited, Slough, Berkshire (GB)

( * ) Notice: Subject to any disclaimer, the term of this patent is extended or adjusted under 35 U.S.C. 154(b) by 0 days.

(21) Appl. No.: 13/120,668

(22) PCT Filed: Sep. 28, 2009

(86) PCT No.: PCT/GB2009/002314
§ 371 (c)(1),
(2), (4) Date: Jun. 6, 2011

(87) PCT Pub. No.: WO2010/035015
PCT Pub. Date: Apr. 1, 2010

(65) Prior Publication Data
US 2012/0016379 A1   Jan. 19, 2012

(30) Foreign Application Priority Data
Sep. 29, 2008 (GB) .................................. 0817794.1

(51) Int. Cl.
*A61B 17/50* (2006.01)
(52) U.S. Cl.
USPC ........................................................ 606/131
(58) Field of Classification Search
USPC ................. 132/76.4, 76.5; 241/273.1–237.3; 451/538, 539, 552, 557, 558; 606/80, 131, 606/167, 186, 189
See application file for complete search history.

(56) References Cited

U.S. PATENT DOCUMENTS

| | | | |
|---|---|---|---|
| 2002/0042589 A1* | 4/2002 | Marsoner | 604/46 |
| 2005/0061343 A1 | 3/2005 | Ebner | |
| 2006/0195110 A1 | 8/2006 | White | |
| 2007/0156124 A1* | 7/2007 | Ignon et al. | 606/9 |
| 2007/0240730 A1 | 10/2007 | Ortiz | |
| 2007/0244491 A1 | 10/2007 | Russell | |
| 2008/0230081 A1 | 9/2008 | Moon | |
| 2011/0196374 A1 | 8/2011 | Porte | |

FOREIGN PATENT DOCUMENTS

| | | |
|---|---|---|
| FR | 0851701 A1 | 9/2009 |
| FR | 2928533 A | 9/2009 |
| WO | 03/022175 A | 3/2003 |
| WO | 2006/068638 A | 6/2006 |
| WO | 2007/020417 A | 2/2007 |
| WO | 2009/122085 A2 | 10/2009 |

OTHER PUBLICATIONS

The ISR for PCT/GB2009/002314.
The Written Opinion for PCT/GB2009/002314.

* cited by examiner

*Primary Examiner* — Ryan Severson
*Assistant Examiner* — Ashley Fishback
(74) *Attorney, Agent, or Firm* — Ryan A. Schneider; Troutman Sanders LLP

(57) ABSTRACT

A hand held device for removing hard skin from calluses comprises a handle (1) and a cutting head (2) having a base plate (8), and several tubular cutting elements (10) inclined so that their cutting edges lie in inclined planes at an angle of 5° to 45° to a skin contact plane defined by the extremities of the cutting elements. The cutting elements can be arranged in an array of staggered rows.

21 Claims, 4 Drawing Sheets

SKIN TREATING DEVICE

CROSS-REFERENCE TO RELATED APPLICATIONS

This application claims the benefit of International Application No. PCT/GB2009/002314, filed 28 Sep. 2009, which claims the benefit of GB 0817794.1, filed 29 Sep. 2008.

FIELD OF THE INVENTION

This invention relates to a device for removing hard skin, particularly unsightly hard skin such as calluses, from the feet or hands.

BACKGROUND OF THE INVENTION

Calluses are areas of thickened skin that may occur on the hands or feet and can be caused by persistent rubbing or uneven pressure, for example from ill-fitting shoes. They have a tendency to form over bony prominences and with regards the feet, they are most commonly found at the heel, the ball of the foot and the sides of the toes. On the hand they typically form on the underside of the fingers or on the palm. Calluses are often unsightly, and the thicker they are the more yellow they can look. With time, particularly thick calluses can become cracked and painful.

There are a number of known methods for reducing or removing calluses, generally based upon rubbing, scraping or cutting the hardened skin away. In many cases this may include a first step of softening the skin by soaking the feet or hands in water or by applying some form of softening lotion to the hard skin. The hard skin can be reduced or removed using a device with an abrasive surface, such as a pumice stone, emery board or a device with carborundum paper attached to it. These devices can be manual or electrically operated and in the latter case, an abrasive head can be vibrated and rotated over the hard skin. Examples of such devices are described in WO03/022175.

The known abrasive devices have a number of drawbacks. In many cases they are unable to conform to the curvature of the parts of the hands or feet where calluses usually occur. In addition, abrasive surfaces tend to wear out with time and they can be difficult to clean, potentially leading to hygiene issues.

The majority of the prior art devices which remove skin with a cutting action incorporate one or more flat metal blades, such as a razor blade or the like. U.S. 2005/0061343 discloses an example of such a cutting device in which a cutting blade is mounted in a head piece attached to a handle in order to be placed in contact with the skin and pulled across the callus for removing a thin layer of skin, the process being repeated as required. Such devices which shave off layers of skin are difficult for untrained people to use safely and often do not discriminate well between callused and healthy skin, so that they can present a significant risk of injury, e.g. due to cutting as a result of the blade being positioned incorrectly or being manipulated so that too much skin is removed.

Some known cutting devices are equipped with one or more curved blades instead of flat blades, the idea being that curved blades will conform more closely to the shaped surface of the foot or hand. An example of such device is described in U.S. 2007/0244491. There are also known callus removers with blades in the form of rasp foils which have a resemblance to cheese graters. These devices are subject to the same drawbacks as outlined above for devices with flat blades.

Another approach to a callus-cutting device is described in U.S. 2007/0240730 and consists of a single stainless steel tube, one end of which is sharpened at its inner edge to provide a circular cutting edge. This callus remover is used by holding the tube perpendicular to the skin and moving the cutting edge back and forth with a reciprocating action for scraping off hard skin. The device is small and difficult to handle. Also, although the scraping effect is optimum when the tube is held perpendicular to the skin, users tend to hold it at an angle, which can make it ineffective or lead to excessive cutting depth.

In U.S. 2008/0230081 there is described a device for removing hard layers of skin, having a body in the form of a disc with several concentric blade edges integrally formed on one side. One embodiment includes a number of such discs disposed in a rectangular array on one side of a planar member having a handle attached at one end, this device being made by injection moulding. The effectiveness of the individual blade edges is impaired due to the proximity and large number of blade edge portions that are configured to contact the skin at the same time.

BRIEF SUMMARY OF THE INVENTION

The present invention aims to eliminate or at least reduce the drawbacks of the prior art devices for removing hard skin, and in accordance with this objective the present invention provides a hand-held device for removing hard skin comprising a handle portion and a cutting head connected firmly to the handle portion to be moved across a skin surface thereby, the cutting head comprising a base, and at least two cutting elements projecting from the base in spaced relationship to each other and each defining a substantially annular cutting edge for contact with a skin surface to be treated, wherein each cutting edge lies in a plane which is inclined to a skin contact plane defined by the extremities of the cutting elements.

The device of the invention provides effective hard skin removal and is also easy and safe to use, even for unskilled users. It incorporates two or more cutting elements that are conveniently formed by stainless steel tubes, each tube having a cutting edge at the skin-contacting end. With the cutting edges inclined to the skin contact plane there can be a small contact area between the cutting edges and the skin so a small force can be used to press the cutting elements against the skin. Also, with there being at least two, and preferably several cutting elements the force with which the device is pressed against the skin by a user is spread over a number of contact points or areas which tend to increase with the force due to the inclination of the planes of the cutting edges, so that the risk of an individual cutting edge being applied with excessive force and possibly cutting too deeply into the skin is substantially reduced. Thus the device of the invention is safe for use by unskilled as well as experienced users because there is less risk of inadvertent injury due to an individual cutting element being applied with sufficient force to cut to an excessive cutting depth.

Each cutting edge lies in a plane inclined to the skin contact plane that contains the extremities of the cutting elements and can be substantially parallel to the base.

The direction of inclination is such that the leading portion of the annular cutting edge is at the greatest distance from the skin contact plane. The inclination of the planes of the cutting edges to the skin contact plane can be from 5° to 45°, such as from 10° to 25°, and in the particular embodiment specifically described herein below is about 15°.

The cutting elements are conveniently tubular, and more especially right circular cylindrical tubes with the cutting edge of each tube lying in a plane perpendicular to the tube axis. The cutting elements can be arranged to project from the base along parallel axes. Although other constructions can easily be envisaged, for convenience of manufacture the base is preferably formed as a plate, for example moulded from rigid plastics material, and provided with sockets to receive the respective cutting elements which can be fixed to the base by being pushed into the sockets with a tight friction fit.

The exact number of cutting elements is not critical, but in the interest of efficiency it is preferable for there to be at least three, and even more preferably at least five, and in any case for the cutting elements to be disposed in a staggered array so that skin missed by the leading cutting elements passing over the skin first may be acted upon by another cutting element that follows. One suitable arrangement is for three cutting elements to be positioned at the corners of a triangle with the apex of the triangle being directed either forwardly or backwardly. Another possibility is for four cutting elements to be positioned at the corners of a diamond shape. Especially effective is an arrangement in which the cutting elements are positioned in at least two rows extending transversely to the movement direction, the cutting elements in one row being staggered with respect to the cutting elements of another row. Thus, five cutting elements can be arranged with three in a first row, and two in a second row so as to cover the gaps between the cutting elements in the first row. According to a preferred embodiment there are at least eight cutting elements arranged in at least three rows; there can be, for example, a first row with at least four cutting elements, a second row with at least three cutting elements and a third row with at least one cutting element. The rows of cutting elements may extend along straight, V-shaped or curved lines. An effective arrangement of cutting elements has been found to be one in which the numbers of cutting elements in successive rows reduces from front to rear along the movement direction.

Suitably the number of cutting elements is not more than twelve, and more preferably not more than ten.

For ease of skin debris clearance it is preferred that the interiors of the tubular cutting elements are connected via openings in the base to a cavity in the device, which cavity is preferably open to the exterior of the device, although it could be closed by a cover that can be opened for rinsing and cleaning purposes. The cavity can be suitably formed by a lateral through opening in the device.

The handle portion may be shaped to facilitate gripping in the hand and while it could have a rounded form for holding in the palm of the hand an elongate shape is preferred, ideally with the axis extending substantially parallel to the skin contact plane of the cutting elements, which facilitates movement of the cutting elements across a hard skin area by pulling on the handle. An especially simple construction that enables economic manufacture has a handle formed by two half shells that are fastened together, such as by adhesive, fasteners, or welding, with the base of the cutting head being separately formed and held firmly in position therebetween.

BRIEF DESCRIPTION OF THE DRAWINGS

The above and other features and advantages of the invention will become apparent from the following description of some preferred embodiments, which is given by way of example and with reference to the accompanying drawings, in which.

DETAILED DESCRIPTION OF PREFERRED EMBODIMENTS

Figure 1:
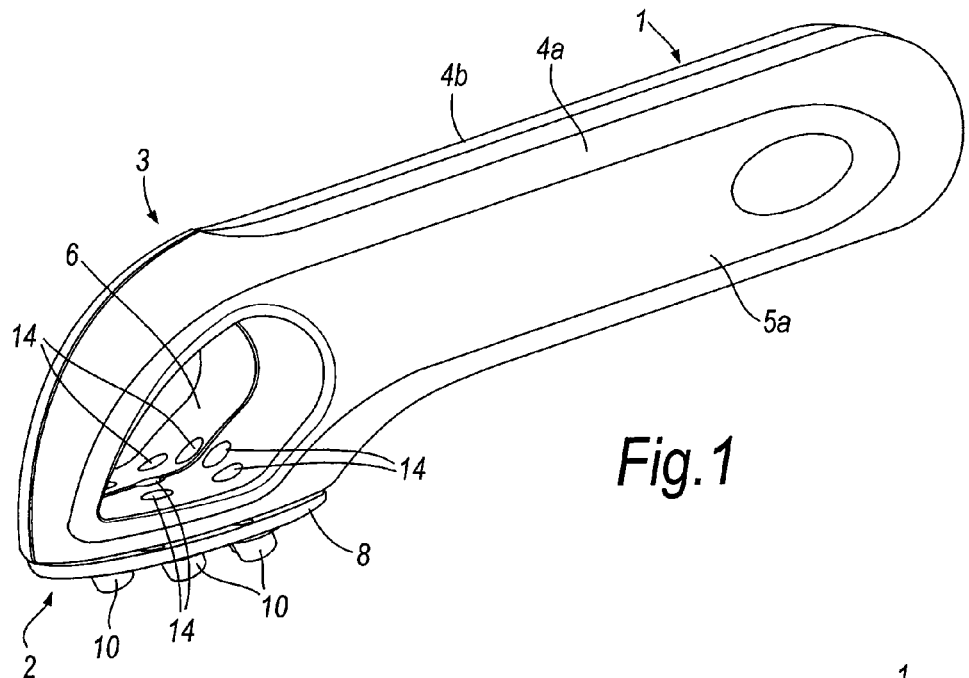
FIG. 1 is a perspective view of a hand-held device according to the invention.
Figure 2:
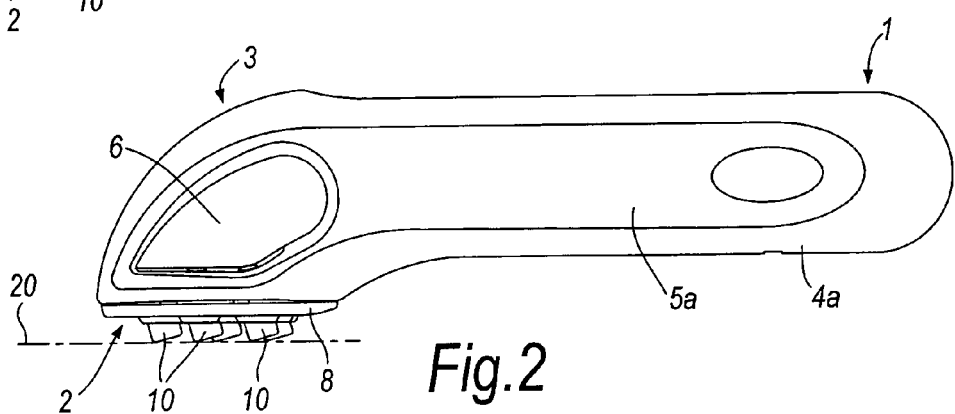
FIG. 2 is a side elevation of the device shown in FIG. 1.
Figure 3:
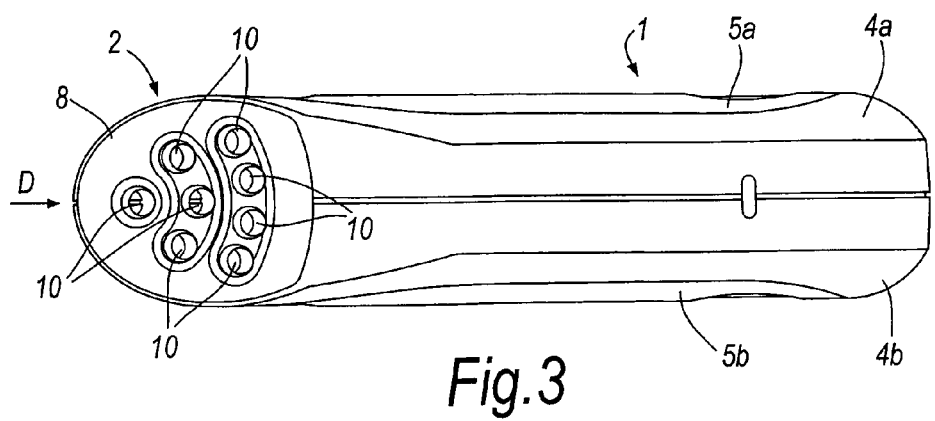
FIG. 3 is an underneath plan view of the device shown in FIG. 1.

Illustrated in FIGS. 1 to 7 of the drawings is a device in the form of a hand tool for removing hard skin, such as calluses on the feet or hands of a user of the device. The device comprises an elongate handle 1 at one end of which is provided a working or cutting head 2. The device has a main body that includes the handle 1 and a cutting head support structure 3, this main body being assembled from two half shells 4a, 4b that are joined firmly and securely together along a longitudinal mid-plane of the device, such as by ultrasonic welding. To enhance comfort in use, the half shells 4a, 4b are provided with panels of softer material 5a, 5b conveniently moulded onto the half shells. The assembled main body includes a cavity 6 formed by a lateral through opening in the cutting head support structure 3, the purpose of which will be explained later.

Figure 4:
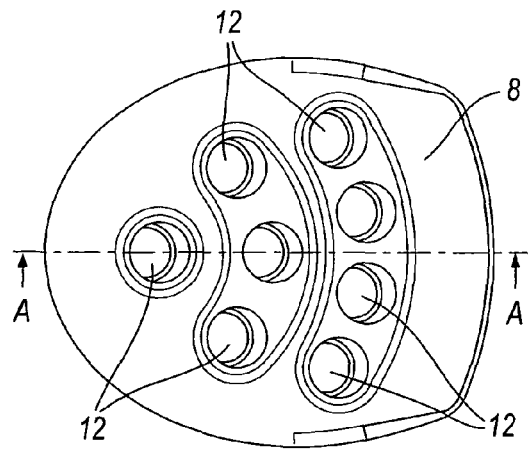
FIG. 4 is a bottom view of the base plate of the cutting head of the device shown in FIG. 1.
Figure 5:
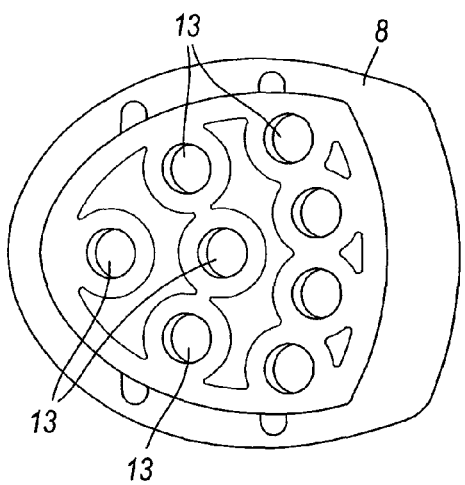
FIG. 5 is a top view of the base plate of FIG. 4.
Figure 6:
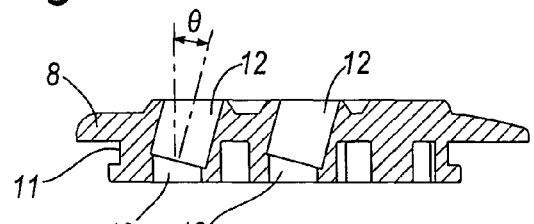
FIG. 6 is a longitudinal cross-section through the base plate taken along the line A-A in FIG. 4.

The cutting head 2 is held fixed in position between the two half shells 4a, 4b when they are assembled and secured together, the cutting head comprising a base plate 8, conveniently injection moulded from rigid plastics material such as ABS, and several cutting elements 10 in the form of stainless steel tubes fixedly fitted to the base plate 8. As shown in FIGS. 4-6, the base plate 8 is substantially flat and is configured with a peripheral groove 11 for receiving an edge flange that extends around a pocket provided in the head support structure 3 to receive the base plate 8, and which flange securely retains the base plate in position on the head support structure 3. The base plate 8 is also formed with an array of sockets 12 adapted to receive the respective tubular cutting elements 10, the inner ends of the sockets being connected to through holes 13 that are open to the inner side of the base plate and register with corresponding holes 14 in the inner wall of the pocket into which the base plate is fitted so that the sockets are connected to the cavity 6 via the holes 13 and 14. The sockets 12 are cylindrical and have their axes parallel and inclined at an angle θ of about 15° to a perpendicular to the plane of the base plate. The sockets 12 are disposed for mounting the cutting elements 10 in a predetermined array further described below.

Figure 7:
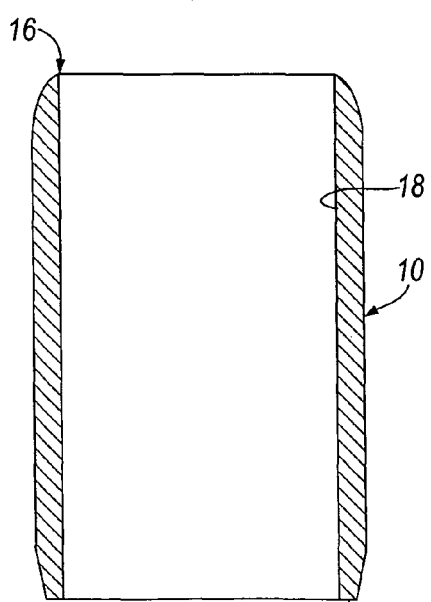
FIG. 7 is an enlarged scale axial cross-section through one of the eight cutting elements fitted into the device shown in FIG. 1.
Figure 8A:
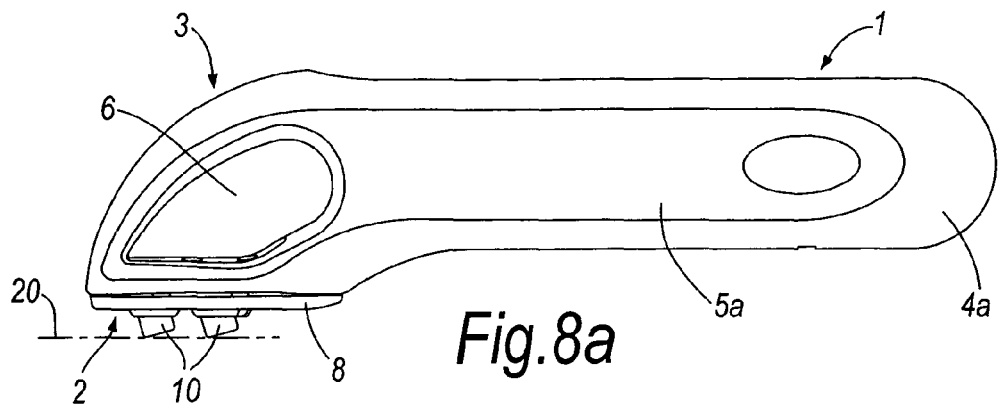
FIGS. 8a and 8b are a side elevation and an underneath plan view, respectively, showing a second embodiment of the invention.
Figure 8B:
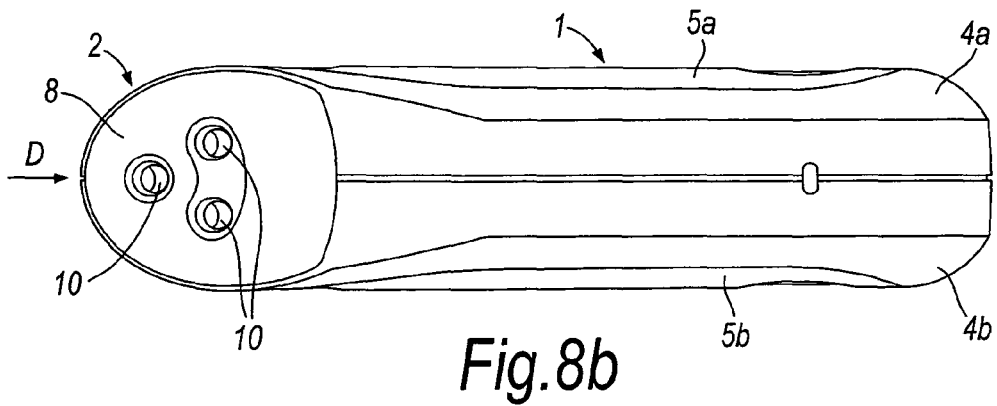
Figure 9A:
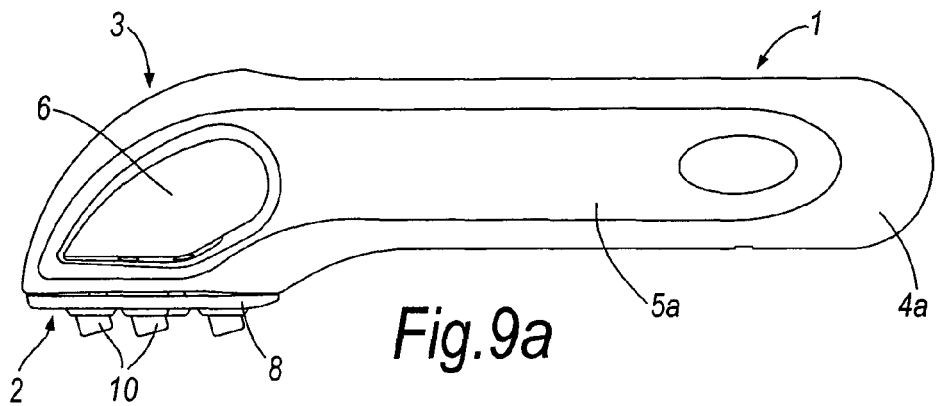
FIGS. 9a and 9b are a side elevation and an underneath plan view, respectively, showing a third embodiment of the invention.
Figure 9B:
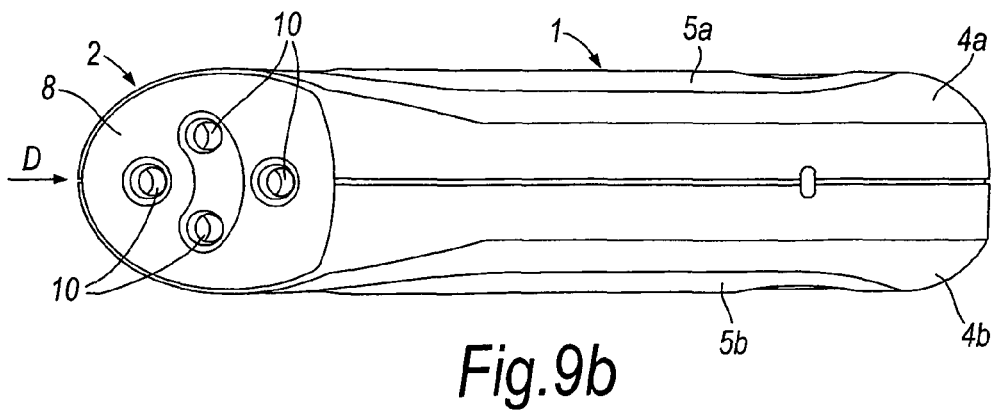
Figure 10A:
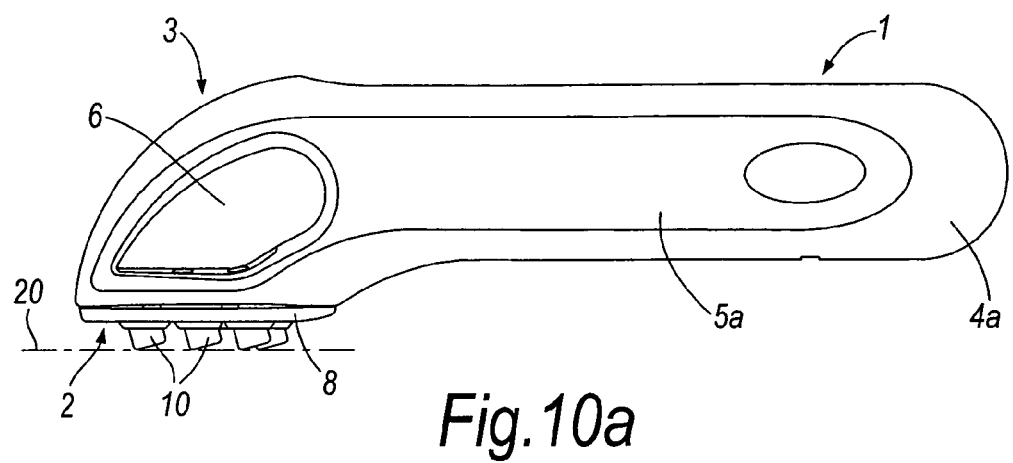
FIGS. 10a and 10b are a side elevation and an underneath plan view, respectively, showing a fourth embodiment of the invention.
Figure 10B:
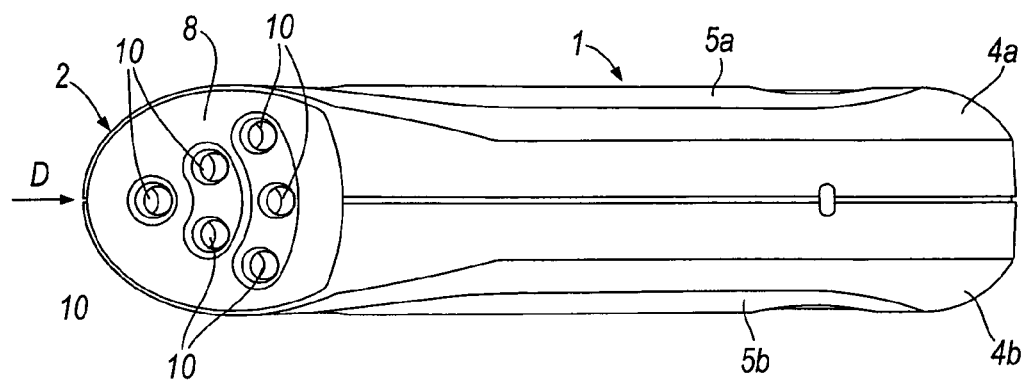

Each cutting element 10 consists of a right circular cylindrical stainless steel tube as shown in cross-section in FIG. 7. At the outer end each tube is tapered to define a circular cutting edge 16 at the end of the inner surface 18 of the tube. The inner end of the tube is chamfered to assist insertion into a socket 12 of the base plate 8, but has a blunt end face 17. The tubes 10 are dimensioned with an outer diameter slightly greater than the diameter of the sockets 12 and the tubes 10 are pushed into the sockets so that they are retained securely by the resulting tight friction fit. With cutting tubes fully inserted into the eight sockets 12 of the base plate, the tubes are set coaxially with the sockets and as a result the cutting edge 16 of each tube 10 lies in an inclined plane that is at an angle of 15° to the contact plane 20 defined by the extremities of the cutting tubes 10.

The pattern of the sockets 12 in the base plate is such that the cutting tubes 10 are disposed in an array with three rows, there being four cutting tubes in the first row, three in the second row and one in the third row, the cutting tubes of the second row being staggered relative to those of the first row so as to span the gaps, between the cutting tubes of the first row. In this way it can be ensured that there will be no skin areas that are located between other skin areas acted on by cutting elements and that will not be themselves acted on by a cutting element when the device is applied to and moved across the skin. As shown the cutting elements 10 in each of the first and second rows are spaced apart along curved lines transverse to the direction of movement D, but this is not essential and other configurations can readily be envisaged. Indeed many different arrays for the cutter tubes on the base plate are possible.

The hollow interiors of the tubular cutting elements 10 are connected to the cavity 6 in the device so that particles of hard skin that are removed by the cutting and scraping action of the cutting edges and which may collect in the tubes can be easily emptied out of the device, and such cleaning can be aided further by rinsing with water.

The inclination of the cutting elements, means that the plane of the cutting edge of each element will be inclined at an angle from 5° to 45°, specifically 15° in the specific embodiment, to the surface of a skin callus being treated with the device, which will ensure very effective skin removal when the device is pulled by means of the handle 1 across the callus with the cutting elements in contact with the skin surface. An appropriate diameter for the circular cutting edges is from 3 to 5 mm, such as around 4 mm.

The hand-held devices for removing hard skin illustrated in FIGS. 8a and 8b, 9a and 9b, and 10a and 10b differ from that described above with reference to FIGS. 1 to 7 only by the number and arrangement of tubular cutting elements (10) provided. The embodiment of FIGS. 8a and 8b has three inclined cutting elements with two in a first row and located on opposite sides of a centre line, and one in a second row and located on the centre line. The device shown in FIGS. 9a and 9b has four cutting elements, with three being positioned as described with reference to FIGS. 8a and 8b and a further cutting element being position on the centre line in front of the row of two cutting elements. The device of FIGS. 10a and 10b has six cutting elements with three positioned as described with reference to FIGS. 8a and 8b, and the other three disposed in an extra row located in front of the row of two cutting elements. In this embodiment the cutting elements in the second row are staggered with respect to those of the first row, and that of the third row is staggered with respect to those of the second row. For further details of the embodiments of FIGS. 8, 9 and 10 reference should be made to the above description relating to the embodiment of FIGS. 1 to 7.

Modifications and further features are possible within the scope of the invention as defined by the claims that follow and will be apparent to those skilled in the art.

The invention claimed is:

1. A hand-held hard skin removing device for removing hard skin comprising a handle portion and a cutting head connected firmly to the handle portion to be moved across a skin surface thereby, the cutting head comprising a base, and at least two cutting elements projecting from the base and each defining a respective substantially annular cutting edge for contact with a skin surface to be treated, wherein the cutting elements are spaced apart from each other, and each cutting edge lies in a plane inclined to a skin contact plane containing the extremities of the cutting elements, wherein the base comprises a base plate having at least two sockets into which the cutting elements are disposed, and the axes of the sockets are parallel to each other and inclined with respect to a perpendicular to the plane of the base plate.

2. A hand-held device according to claim 1, wherein the inclined plane is at an angle in the range of from 5° to 45° to the skin contact plane.

3. A hand-held device according to claim 1, wherein the cutting elements are tubular.

4. A hand-held device according to claim 3, wherein the cutting elements are right circular cylindrical tubes, and the cutting edge of each cutting element lies in a plane perpendicular to the axis of the cutting element.

5. A hand-held device according to claim 1, wherein the cutting elements project from the base along parallel axes.

6. A hand-held device according to claim 1, wherein there are three or more cutting elements positioned in a staggered array.

7. A hand-held device according to claim 6, wherein the cutting elements are arranged in at least two rows extending transversely to a movement direction, the cutting elements in one row being staggered with respect to the cutting elements of another row.

8. A hand-held device according to claim 7, wherein there are at least eight cutting elements arranged in at least three rows.

9. A hand-held device according to claim 7, wherein a first row includes at least four cutting elements, a second row includes at least three cutting elements and a third row includes at least one cutting element.

10. A hand-held device according to claim 7, wherein the cutting elements of at least one row are spaced apart along a curved line.

11. A hand-held device according to claim 7, wherein the base has a front in proximity to the handle, and a rear distal the handle, the numbers of cutting elements in successive rows reducing from front to rear of the base.

12. A hand-held device according to claim 1, wherein the base comprises a base plate to which the cutting elements are fixed.

13. A hand-held device according to claim 12, wherein the base plate has sockets into which the respective cutting elements are inserted.

14. A hand-held device according to claim 13, wherein the sockets have inner ends that are open to a cavity within the device.

15. A hand-held device according to claim 14, wherein the cavity is open to the exterior of the device.

16. A hand-held device according to claim 15, wherein the cavity is formed by a lateral through opening in the device.

17. A hand-held device according to claim 1, wherein the handle portion is elongated.

18. A hand-held device according to claim 17, wherein the handle portion has an axis substantially parallel to a skin contact plane defined by the extremities of the cutting elements.

19. A hand-held device according to claim 1, wherein the inclined plane is at an angle in the range of from 10° to 25° to the skin contact plane.

20. A hand-held device to claim 1, wherein there are five or more cutting elements positioned in a staggered array.

21. A hand-held device according to claim 1, wherein the cutting elements are right circular cylindrical tubes having a diameter of 3 mm to 5 mm.

\* \* \* \* \*